United States Patent [19]

Vedres et al.

[11] Patent Number: 4,960,888
[45] Date of Patent: Oct. 2, 1990

[54] PREPARATION OF 6-AMINO-1,2-DIHYDRO-1-HYDROXY-2-IMINO-4-PIPERIDINOPYRIMIDINE COMPOUNDS

[75] Inventors: András Vedres; Csaba Szántay; Béla Stefkó; János Kreidl; András Nemes; Gábor Blaskó; Erik Bogsch; Dénes Máthé; István Hegedüs; Adrien Szuchovszky, née Gergely; Tamás Mester, all of Budapest, Hungary

[73] Assignee: Richter Gedeon Vegyeszeti Gyar R.T., Budapest, Hungary

[21] Appl. No.: 320,875

[22] Filed: Mar. 9, 1989

Related U.S. Application Data

[62] Division of Ser. No. 72,009, Jul. 10, 1987, abandoned.

[30] Foreign Application Priority Data

Jul. 10, 1986 [HU] Hungary .............. 2855/86

[51] Int. Cl.[5] .......................... C07D 239/34
[52] U.S. Cl. ................................. 544/323
[58] Field of Search ..................... 544/324, 373

[56] References Cited

U.S. PATENT DOCUMENTS 3,644,364  2/1972  Anthony .................. 540/601
3,998,827 12/1976  Thomas, Jr. et al. ..... 544/323
4,549,019 10/1985  Muller et al. ........... 544/320

OTHER PUBLICATIONS

Fessenden et al, *Organic Chemistry*, 1982, pp. 614–615.

Primary Examiner—John M. Ford
Assistant Examiner—Zinna Northington-Davis
Attorney, Agent, or Firm—Keil & Weinkauf

[57] ABSTRACT

The invention relates to a new process for preparing 6-amino-1,2-dihydro-1-hydroxy-2-imino-4-piperidinopyrimidine of the formula (I),

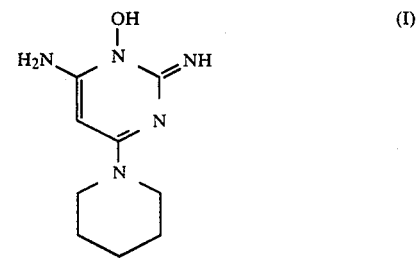

which comprises reacting a pyrimidine derivative of the general formula (II),

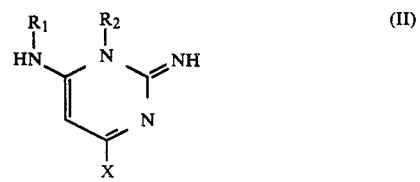

wherein
R$_1$ stantds for hydrogen or a

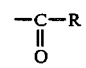

group, wherein
R means a C$_{1-6}$ alkyl group or an aryl group optionally substituted by halogen;
R$_2$ stands for a hydroxyl group or an

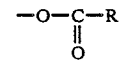

group, wherein
R is as defined above; and
X represents chlorine or bromine or an optionally mono- or polysubstituted arenesulfonyloxy group, with the proviso that R$_2$ is different from a hydroxyl group when R$_1$ stands for hydrogen, with piperidine and hydrolyzing, optionally after isolation, the thus-obtained 4-piperidino derivative of the general formula (III),

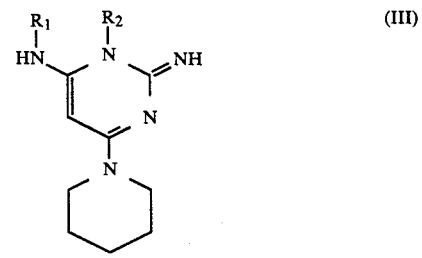

wherein R$_1$ and R$_2$ are as defined above.

7 Claims, No Drawings

PREPARATION OF 6-AMINO-1,2-DIHYDRO-1-HYDROXY-2-IMINO-4-PIPERIDINOPYRIMIDINE COMPOUNDS

This application is a continuation of application Ser. No. 072,009, filed on July 10, 1987 now abandoned.

The invention relates to a new process for preparing 6-amino-1,2-dihydro-1-hydroxy-2-imino-4-piperidinopyrimidine of the formula (I).

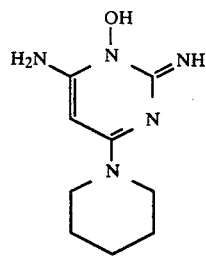

Being an excellent antihypertensive agent Drugs 22, 257 (1981), the compound of the formula (I) (generic name: minoxidil) is the active ingredient of a number of blood pressure lowering compositions commercially available in many countries.

In the recent years, the utilization of the compound of formula (I) as a therapeutical cosmetic has become more and more conspicuous since it effectively stimulates hair growth in an externally used dilute solution Pharm. Ind. 46, 937 (1984); ibidem 47. 506 (1985).

Owing to its two possible tautomeric forms, minoxidil has two chemical names in the literature: in the Chemical Abstracts, it has been named 6-amino-1,2-dihydro-1-hydroxy-2-imino-4-piperidinopyrimidine up to 1972 and 6-(1 piperidinyl)-2,4-pyrimidinediamine-3-oxide after 1972. In the present patent application the first name is used by which the chemical principle of our preparation process is better reflected; it should be understood, however, that our process relates to the preparation of both tautomeric forms.

Although several methods have been described for preparing the compound of formula (I), owing to the low yields and the poor availability of the starting materials, none of them can be considered to be an effective and economical process useful at an industrial scale.

First the substance of the formula (I) was synthetized from 4-chloro 2,6-diaminopyrimidine British patent specification No. 1,167,735; CA. 68, 21947h by heating the latter compound with 2,4-dichlorophenol at 150° C. in the presence of 85% aqueous potassium hydroxide solution to give 2,6-diamino-4-(2,4-dichlorophenoxy)-pyrimidine. This substance was oxidized in a low yield to 6 amino 4-(2,4 dichlorophenoxy)-1,2-dihydro-1-hydroxy-2-iminopyrimidine, which was then transformed at 150° C. with piperidine to the target compound of the formula (I). The overall yield of this synthesis amounts to about 2.5% with a 45% yield in the last step. This is mainly caused by the fact that the replacement of the 2,4-dichlorophenoxy group by piperidine requires severe reaction conditions and long heating periods which favour unrequired side reactions, too.

An other method J. Org. Chem. 41, 3304 (1975) cannot be considered to be useful for industrial realization either because specific conditions (exclusion of moisture, very low temperature) and difficultly available, expensive substances ("magic methyl", trimethyloxonium fluoborate) are required to carry out the key step of the synthesis comprising the activation of the acid amide carbonyl group of cyanoacetylpiperidine.

The synthesis of the compound of formula (I) has been achieved in somewhat better yields by other known processes. According to the published German patent application No. 2,114,887, 6-amino-4-chloro-1,2-dihydro-1-hydroxy-2-iminopyrimidine is used as starting material, whereas the corresponding 4-(p-toluenesulfonyloxy) derivative is described as starting substance in the Hungarian patent specification No. 177,601. According to the Examples of this Hungarian patent specification, the reaction can be carried cut in a yield of 55 to 65%. A further improvement in the yield is hampered, however, by the relatively long reaction period and high temperature favouring even here the formation of side products. The target compound becomes contaminated by the side products arising from the damage of the free amino groups of the molecule, whereby a further purification is required to achieve appropriate purity. Another drawback of the above processes is that the starting substances are prepared by the rather complicated method of oxidizing with perbenzoic or m-chloroperbenzoic acid.

Thus, the aim of the present invention is to provide an economically practicable synthesis of the compound of formula (I), which renders possible to easily produce this compound in a good yield and in a high purity at an industrial scale, too.

According to the invention, 6 amino 1,2-dihydro-1-hydroxy-2-imino-4-piperidinopyrimidine of the formula (I) is prepared by reacting a pyrimidine derivative of the general formula (II),

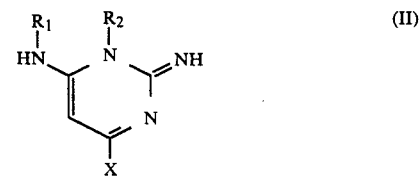

wherein
$R_1$ stands for hydrogen or a

group, wherein
R means a $C_{1-6}$ alkyl group or an aryl group optionally substituted by halogen;
$R_2$ stands for a hydroxyl group or an

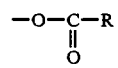

group, wherein
R is as defined above; and
X represents chlorine or bromine or an optionally mono- or polysubstituted arenesulfonyloxy group,
with the proviso that $R_2$ is different from a hydroxyl group when $R_1$ stands for hydrogen, with piperidine and hydrolyzing, optionally after isolation, the thus-obtained 4-piperidino derivative of the general formula (III)

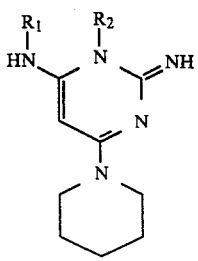

wherein $R_1$ and $R_2$ are as defined above.

X defined as an "optionally mono- or polysubstituted arenesulfonyloxy group" in the general formula (II) preferably means a benzenesulfonyloxy group substituted by one or more $C_{1-3}$ alkyl group(s), preferably by a methyl group on the benzene ring. Preferred representatives of such groups are the tosyloxy and mesitylenesulfonyloxy group. Most preferably, X means chlorine.

The meaning "$C_{1-6}$ alkyl group" of R in the definition of $R_1$ and $R_2$ in the general formulae (II) and (III) may mean any $C_{1-6}$ straight or branched chain, saturated hydrocarbyl group such as methyl, ethyl, n-propyl, isopropyl, n-butyl, secondary and tertiary butyl, n-pentyl, isopentyl, n-hexyl and isohexyl group, preferably $C_{1-4}$ alkyl group and more preferably methyl group.

R as an aryl group may represent any $C_{6-12}$ aryl, preferably phenyl, group optionally substituted by one or more halogen(s), preferably by one or more chlorine atom(s)

The pyrimidine derivatives of the general formula (II) used as starting materials in the process of the invention are new compounds which can be prepared by reacting an appropriate 2,6-diaminopyrimidine derivative substituted by a suitable X group in position 4 with an appropriate acid anhydride in the presence of water and hydrogen peroxide. This process has been described in our simultaneously filed Hungarian patent application No. 2856/86.

The key step of the process of the invention is the nucleophilic substitution reaction of the compounds of the general formula (II) with piperidine, which readily proceeds under mild conditions owing to the electron-attracting properties of the acyl or acyloxy groups defined as $R_1$ or $R_2$, respectively. The temperature of this reaction as depending on other conditions, such as the solvent, is 0° to 100° C., preferably room temperature. The reaction proceeds within a period lasting from 5 minutes to several hours; at room temperature at most 2 hours are usually enough for completing this reaction, whereas this period can substantially be abbreviated by increasing the reaction temperature. An excess of piperidine may serve as solvent of this reaction, though other solvents such as protic solvents, e.g. ethanol; dipolar aprotic solvents, e.g. acetonitrile; or apolar aprotic solvents, e.g. chloroform may also be used. Under such conditions, the yield of the 4-piperidino derivative of the general formula (III) is practically quantitative.

It is surprisingly easy to remove by hydrolysis the acyl or acyloxy groups, e.g. the acetyl or acetoxy group defined as $R_1$ or $R_2$, respectively, from the thus obtained 4-piperidino derivatives of the general formula (III). On using piperidine as solvent, this reaction rapidly proceeds even at room temperature in such a way that the derivatives containing the acyl or acyloxy group, respectively, cannot even be isolated; or, it proceeds within a few minutes under the conditions of the working-up, under the effect of water and a base, e.g. on the effect of an aqueous alkali metal hydroxide solution. This process, however, may also be carried out in such a way that the intermediate product of the general formula (III) is isolated in a high yield and purity.

The compound of the formula (I) obtained as a result of the process of the invention is isolated in a crystalline form and high purity without any detectable side products.

The drawbacks of the known processes for preparing the compound of the formula (I) are eliminated by using the process of the invention.

The most important advantages of the process of the invention can be summarized as follows:

The starting compounds of the general formula (II) can easily be prepared in a high yield by using the process described in our simultaneously filed Hungarian patent application No. 2856/86.

The starting materials are more reactive than any starting substance known in the prior art. This is due to the electron-attracting properties of the acyl or acyloxy groups, respectively, whereby the electron density in position 4 of the pyrimidine ring is decreased and thus the nucleophilic substitution by piperidine proceeds more readily.

The most sensitive sites of the molecule are simultaneously protected by the acyl or acyloxy groups, respectively, whereby the process will not be accompanied by any side reaction.

Surprisingly, the acyl and acyloxy groups can very easily be removed, e.g. by hydrolysis with an equivalent amount of an alkali metal hydroxide solution for a few minutes at room temperature. This ready elimination is a structural feature of the molecule, which is due to the N-oxide moiety. The hydrolysis of the acyl group proceeds on the oxygen atom bound to the nitrogen in the 1 position. Any acyl group present in an other position migrates to this position under the effect of acids or alkali metal hydroxides and is hydrolyzed with a rate corresponding to that of the esters.

As a result of all these advantages, the target compound of the formula (I) can be prepared under mild reaction conditions, in a high yield, i.e. in yields of 70 to 80% under the optimum conditions, and in a high purity by using starting substances which are easily available and can also be obtained in a good yield.

The process of the invention is illustrated in detail by the following non-limiting Examples.

EXAMPLE 1

Preparation of 6-amino-1,2-dihydro-1-hydroxy-2-imino-4-piperidinopyrimidine 1.01 g (5 mmoles) of 1-acetoxy-6-amino-4-chloro-1,2-dihydro-2-iminopyrimidine are added under stirring to a mixture containing 10 ml of ethanol and 3 ml of piperidine. The mixture is refluxed while stirring for 30 minutes, then 5 ml of 1N aqueous sodium hydroxide solution are added and the boiling is continued for additional 30 minutes. Thereafter, the mixture is evaporated under reduced pressure and the residue is mixed with 10 ml of water. The crystalline precipitate is filtered, washed with water and dried to give the aimed compound in a yield of 0.85 g (82%), m.p.: 262°–266° C.

IR (cm$^{-1}$) 3450, 3420, 3400, 3370, 3260, 1655, 1250, 1210, 1165, 1020.

$^1$H-NMR (DMSO-d$_6$): 1.52; 3.40; 5.36; 6.84.
$^{13}$C-NMR (DMSO-d$_6$+CD$_3$OD): 156.6; 153.7; 152.1; 74.1; 45.7; 25.7; 24.7.

EXAMPLE 2

Preparation of
6-amino-1,2-dihydro-1-hydroxy-2-imino-4-piperidinopyrimidine 2.02 g (10 mmoles) of 1-acetoxy-6-amino-4-chloro-1,2-dihydro-2-iminopyrimidine are added to 8 ml of piperidine at room temperature while stirring. The mixture is stirred at room temperature for 2 hours, then piperidine is evaporated under reduced pressure. The residue is taken up in a mixture containing 20 ml of ethanol and 10 ml of 1N aqueous sodium hydroxide solution and refluxed for 30 minutes, then evaporated under reduced pressure. The residue is taken up in 20 ml of water, the crystals are filtered, washed with water and dried to give 1.74 g (86% yield) of the aimed compound which shows no melting point depression when mixed with the product of Example 1.

EXAMPLE 3

Preparation of
6-amino-1,2-dihydro-1-hydroxy-2-imino-4-piperidinopyrimidine 0.3 g (0.88 mmole) of 1-acetoxy-6-amino-1,2-dihydro-2-imino-4-(4-toluenesulfonyloxy)pyrimidine is added to a solution containing 10 ml of chloroform and 2 ml of piperidine while stirring. The mixture is refluxed under stirring for 30 minutes, then evaporated under reduced pressure. To the residue, 5 ml of ethanol and 1 ml of 1N aqueous sodium hydroxide solution are added. The mixture is set aside at room temperature for one hour, then evaporated under reduced pressure. The residue is triturated with 10 ml of water, the crystals are filtered, washed with water and dried to give 0.14 g (75% yield) of the aimed compound which shows no melting point depression when mixed with the product of Example 1.

EXAMPLE 4

Preparation of
6-amino-1,2-dihydro-1-hydroxy-2-imino-4-piperidinopyrimidine

After adding 0.49 g (2 mmoles) of 6-acetamido-1-acetoxy-4-chloro-1,2-dihydro-2-iminopyrimidine to a solution containing 10 ml of chloroform and 2 ml of piperidine, the mixture is refluxed for 30 minutes, then evaporated under reduced pressure. The residue is dissolved in the mixture of 10 ml of ethanol and 3 ml of 1N aqueous sodium hydroxide solution. The reaction mixture is left to stand at room temperature for one hour and then again evaporated under reduced pressure. After taking up the residue in 10 ml of water, the crystals are filtered, washed with water and dried to give 0.34 g (80% yield) of the aimed compound which shows no melting point depression when mixed with the product of Example 1.

EXAMPLE 5

Preparation of
6-amino-1,2-dihydro-1-hydroxy-2-imino-4-piperidinopyrimidine 76 g (0.2 mole) of 6-acetamido-1-acetoxy-1,2-dihydro-2-imino-4-(4-toluenesulfonyloxy)pyrimidine are added to 760 ml of anhydrous piperidine at a temperature of 0° to 5° C. while stirring. The mixture is stirred at the same temperature for additional 2 hours, then let to warm to room temperature and stirred for additional 24 hours. The piperidine is distilled off under reduced pressure, 500 ml of water are added to the residue, then the mixture is left to stand in the refrigerator overnight. The precipitate is filtered, washed with water and filtered by strong suction. The filter cake is washed by suspending it 3 times with 50 ml of ether each and dried to give the aimed product in a yield of 23.0 g (55%).

75 ml of 10% sodium hydroxide solution are added to the mother liquor and then the reaction mixture is evaporated under reduced pressure. After adding 200 ml of water to the residue, the pH value of the solution is adjusted to 7. After standing overnight in the refrigerator, the crystals are filtered, washed with water and dried to give an additional yield of 8.9 g (21%) of the aimed compound.

In such a way, a total yield of 31.9 g (76%) of the aimed compound is obtained, which shows no melting point depression when mixed with the product of Example 1.

EXAMPLE 6

Preparation of
6-acetamido-1,2-dihydro-1-hydroxy-2-imino-4-piperidinopyrimidine

After adding 1.01 g (5 mmoles) of 2-acetamido-6-amino-4-chloropyrimidine-1-oxide to the mixture of 20 ml of chloroform with 5 ml of piperidine, the solution is refluxed while stirring for 30 minutes. After cooling down, the solution is extracted 3 times with 10 ml of 1N hydrochloric acid each, then washed 3 times with 10 ml of water each. The chloroformic phase is dried over anhydrous sodium sulfate and evaporated under reduced pressure. The residue is thoroughly triturated with 50 ml of ether, the crystals are filtered, washed with ether and dried to give the aimed compound in a yield of 0.86 g (69%), m.p.: 204°–205° C.

IR (KBr, cm$^{-1}$) 1670, 1600, 1570, 1500.
UV (ethanol, nm): 245, 325.
$^1$H-NMR (CDCl$_3$+CD$_3$OD): 1.63, (m, 6H), 2.30 (s, 3H), 3.57 (m, 6H), 7.04 (s, 1H).

EXAMPLE 7

Preparation of
6-acetamido-1-acetoxy-1,2-dihydro-2-imino-4-piperidinopyrimidine

A mixture containing 0.5 g (0.0013 mole) of 6-acetamido-1-acetoxy-1,2-dihydro-2-imino-4-(4-toluenesulfonyloxy)pyrimidine in 20 ml of acetonitrile and 0.5 ml of piperidine is stirred at room temperature for 3 hours, then evaporated under reduced pressure. After adding 30 ml of ether to the residue, the crystalline precipitate is filtered, washed with ether and then with water, finally dried to give the aimed product in a yield of 0.24 g (64%), m.p.: 217°–218° C. (with decomposition).

IR (KBr, cm$^{-1}$): 1710, 1680, 1630, 1570, 1530.
UV (ethanol, nm): 241, 293, 323.
$^1$H-NMR (CDCl$_3$+TFA-d): 1.76 (m, 6H), 2.43 (s, 3H), 2.57 (s, 3H), 3.80 (m, 4H), 7.55 (s, 1H).

EXAMPLE 8

Preparation of 6-amino-1,2-dihydro-1-hydroxy-2-imino-4-piperidinopyrimidine 0 5 g (2 mmoles) of 6-acetamido-1,2-dihydro-1-hydroxy-2-imino-4-piperidinopyrimidine prepared as described in Example 6 is dissolved in a mixture containing 10 ml of ethanol and 4 ml of 1N sodium hydroxide solution, the mixture is refluxed for 30 minutes, then evaporated under reduced pressure. After taking up the residue in 10 ml of water, the crystals are filtered, washed with water and dried to give the aimed compound in a yield of 0.35 g (85%), which shows no melting point depression when mixed with the product of Example 1.

EXAMPLE 9

Preparation of 6-amino-1,2-dihydro-1-hydroxy-2-imino-4-piperidinopyrimidine 1.0 g (3.4 mmoles) of 6-acetamido-1-acetoxy-1,2-dihydro-2-imino-4-piperidinopyrimidine prepared as described in Example 7 is dissolved in a mixture containing 20 ml of ethanol and 5 ml of 1N aqueous sodium hydroxide solution, the mixture is refluxed for 30 minutes, then evaporated under reduced pressure. Taking up the residue in 10 ml of water, the crystals are filtered, washed with water and dried to give the aimed compound in a yield of 0.54 g (76%), which shows no melting point depression when mixed with the product of Example 1.

EXAMPLE 10

Preparation of 6-amino-1,2-dihydro-1-hydroxy-2-imino-4-piperidinopyrimidine 2.0 g (0.0093 mole) of 6-amino-4-chloro-1,2-dihydro-2-imino-1-propionyloxy-pyrimidine is boiled in 10 ml of water, in the presence of 3 ml piperidene for 30 minutes, then, after adding 10 ml of 1N aqueous sodium hydroxide solution and 5 ml of water, the solution is refluxed for additional 30 minutes, and then After standing for one hour, the precipitated crystals are filtered and washed with water to give the aimed compound in a yield of 1.36 g (83%).

EXAMPLE 11

Preparation of 6-amino-1,2-dihydro-1-hydroxy-2-imino-4-piperidinopyrimidine

In a 500 ml round-bottom flask fitted with a stirrer and thermometer, 40.8 g (0.1 mole) of crude 6-acetamido-1-acetoxy-1,2-dihydro-2-imino-4-mesitylenesulfonyl oxypyrimidine are reacted with 380 ml (327 g; 3.84 moles) of piperidine under stirring and cooling by ice. After warming up of the reaction mixture to room temperature, the stirring is continued till the disappearing of the starting materials as detected by thin layer chromatography. This lasts about 24 hours. Then piperidine is evaporated under reduced pressue on a bath kept at 60° C. and 250 ml of water are added to the residue. After cooling, the precipitated product is filtered, washed with water and dried on the filter. From the solid filter cake remaining on the filter, the sulfonamide side product is washed out with a little amount of toluene.

After evaporating the toluene solution to dryness, 3.9 g (14.5% yield) of N-mesitylenesulfonyl piperidine are obtained; the substance remaining on the filter, which is the aimed product, amounts to 13 g.

The mother liquor is subjected to a further working up: after adding 38 ml of 10% aqueous sodium hydroxide solution, it is evaporated to oily consistency under reduced pressure, whereby the residual piperidine can be removed. After adding 100 ml of water, the pH value of the solution is adjusted to 7 by adding 10% hydrochloric acid solution. After a prolonged cooling, the precipitate is filtered and washed with water to give additional 5.3 g of the aimed compound.

In such a way, a total yield of 17.9 g (85.5%) of 6-amino-1,2-dihydro-1-hydroxy-2-imino-4-piperidinopyrimidine are obtained, m.p.: 240°–260° C. (with decomposition).

The chromatographic and spectroscopic characteristics of this product are in agreement with those prepared as described in the above Examples.

We claim:

1. A 4-piperidinopyrimidine of the formula

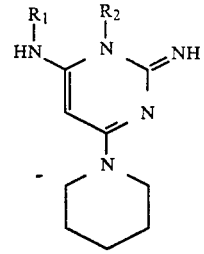

wherein
$R_1$ is hydrogen or a

group, wherein
R is a $C_{1-6}$ alkyl group or an unsubstituted or halogen substituted aryl group; and
$R_2$ is an

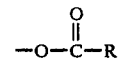

group, wherein
R is as defined above.

2. The compound of claim 1, wherein $R_1$ is

3. 6-acetamideo-1-acetoxy-1,2-dihydro-2-imino-4-piperidinopyrimidine.

4. A process for transforming 6-acetamido-1-acetoxy-1,2-dihydro-2-imino-4-piperidinopyrimidine into 6-amino-1,2-dihydro-1-hydroxy-2-imino-4-piperidinopyrimidine comprising: subjecting a compound of the formula

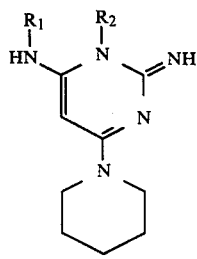

wherein

R₁ is hydrogen or a

group, wherein

R is a $C_{1-6}$ alkyl group or an unsubstituted or halogen substituted aryl group; and R₂ is an

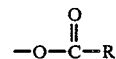

group, wherein
R is as defined above;
to alkaline hydrolysis under mild conditions to produce a compound of the formula

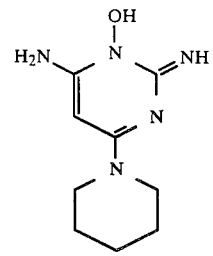

5. The process of claim 4, wherein 6-acetamino-1-acetoxy-1,2-dihydro-2-imino-4-piperidine is subjected to alkaline hydrolysis with an equivalent amount of an alkali metal hydroxide solution.

6. The process of claim 5, wherein said alkali metal hydroxide solution is a sodium hydroxide solution.

7. The process of claim 5, wherein said alkaline hydrolysis occurs at room temperature.

* * * * *